US007014614B2

(12) United States Patent
Casula

(10) Patent No.: US 7,014,614 B2
(45) Date of Patent: Mar. 21, 2006

(54) DEVICE FOR TRANSCUTANEOUS BIOPSY

(75) Inventor: Gianfranco Casula, Rho (IT)

(73) Assignee: H.S. Hospital Service S.P.A., Pomezia (IT)

(*) Notice: Subject to any disclaimer, the term of this patent is extended or adjusted under 35 U.S.C. 154(b) by 363 days.

(21) Appl. No.: 10/333,488

(22) PCT Filed: Jul. 20, 2001

(86) PCT No.: PCT/IB01/01292

§ 371 (c)(1),
(2), (4) Date: Jan. 16, 2003

(87) PCT Pub. No.: WO02/07602

PCT Pub. Date: Jan. 31, 2002

(65) Prior Publication Data
US 2003/0171694 A1  Sep. 11, 2003

(30) Foreign Application Priority Data
Jul. 20, 2000  (IT) .............................. MO00A0159

(51) Int. Cl.
A61B 10/00  (2006.01)

(52) U.S. Cl. ................................................ 600/567
(58) Field of Classification Search ............. 600/566, 600/567, 564, 583; 606/167
See application file for complete search history.

(56) References Cited

U.S. PATENT DOCUMENTS

| 4,200,111 A |   | 4/1980 | Harris |
|---|---|---|---|
| 5,649,547 A | * | 7/1997 | Ritchart et al. ............. 600/566 |
| 6,022,324 A | * | 2/2000 | Skinner ...................... 600/566 |
| 6,063,037 A |   | 5/2000 | Mittermeier et al. |

FOREIGN PATENT DOCUMENTS

| DE | 20010879 | 10/2000 |
|---|---|---|
| WO | WO9627330 | 9/1996 |

* cited by examiner

Primary Examiner—Max F. Hindenburg
Assistant Examiner—Brian Szmal
(74) Attorney, Agent, or Firm—Collard & Roe, P.C.

(57) ABSTRACT

Device for transcutaneous biopsy comprising needle means provided with handle at a proximal end thereof and provided with cutting edge at a distal end thereof, mandrel means which may be inserted into the needle means, the needle means comprising a substantially cylindrical hollow body having a substantially constant inner diameter; the device comprises blocking means suitable for blocking a sample of tissue inside the needle means, the blocking means being slidably coupled inside the needle means.

13 Claims, 9 Drawing Sheets

DEVICE FOR TRANSCUTANEOUS BIOPSY

CROSS REFERENCE TO RELATED APPLICATIONS

Applicant claims priority under 35 U.S.C. §119 of Italian Application No. MO2000A000159 filed Jul. 20, 2000. Applicant also claims priority under 35 U.S.C. §365 of PCT/IB01/01292 filed Jul. 20, 2001. The international application under PCT article 21(2) was published in English.

The present invention concerns a device for transcutaneous biopsy both of soft tissues and of rigid tissues, in particular a device for collecting samples of organic tissue from a patient's body.

In prior art, devices are known of a needle type for transcutaneous biopsy of rigid tissues, comprising a needle having the shape of a hollow cylinder, of variable length and diameter, an end of which, i.e. the so-called proximal end, is provided with a handle, suitable for enabling the operator to hold and operate the needle, whereas the other end, i.e. the so-called distal end is provided with cutting edge, suitable for allowing the separation, at least partial, of the tissue sample to be collected from the encircling tissue.

The needle is equipped with a mandrel consisting of a steel rod whose dimensions are such that the rod can slide inside the needle; said rod is further provided with a sharp end that extends from the distal end of the needle and that is designed to perforate the surface layer, particularly hard, of the bone tissue, so as to reach the medullary tissue.

The biopsy is carried out pushing and rotating the needle through the patient skin and muscles until the sharp end of the mandrel contacts the bone and perforates its surface layer reaching the medullary tissue.

The mandrel is then extracted from the needle and the needle is further pushed inside the medullary tissue, again by means of combined movements of pressure and rotation, so that the cutting distal end of the needle cuts off a roughly cylindrical tissue portion from the encircling tissue and incorporates the tissue portion inside the needle: this tissue portion constitutes the biopsy sample to be collected. The above mentioned sample is still connected to the tissue encircling its distal end, i.e. the end oriented towards the outside of the needle.

In order to produce the separation of the sample distal end from the encircling tissue, the needle is caused to rotate and oscillate in a direction substantially perpendicular to the longitudinal axis thereof and is finally extracted from the patient's body.

However, this operation causes generally a significant trauma for the patient, since the movements given to the needle, particularly the oscillating movements, produce a plurality of micro fractures in the bone tissue, which generate strong suffering in the patient and prolong the recovery time.

Furthermore, there is no assurance that the tissue sample cut off from the encircling tissue is really collected, both since the movements given to the needle may not be enough to break the distal end of the sample, which, in this case, is not separated from the encircling tissue, and since the sample, even if it is separated from the encircling tissue, may partially protrude from the needle, when the needle is extracted, and be thus damaged, or may also protrude completely, and remain thus inside the patient's body. In both the cases, the operation of sample collecting has to be repeated in another position, with consequent remarkable worsening of trauma and suffering caused to the patient.

Furthermore, a device is known for transcutaneous biopsy of rigid tissues, comprising a needle and a mandrel similar to those previously described, wherein the needle is tapered at a distal end thereof. The device is provided with a blocking element to be inserted through the proximal end of the needle, after the needle has been introduced into the patient's body and has incorporated inside a tissue sample to be collected.

The blocking element is shaped so that it may be inserted between an area of the inner wall of the needle and the tissue sample incorporated into the needle. When the blocking element is pushed towards the tapered section at the end of the hollow cylinder, the blocking element is radially inwardly deflected so as to force the tissue sample against the opposite area of inner wall of the hollow cylinder. Thus, the tissue sample remains blocked as an effect of the friction originating between said tissue sample, the blocking element and the needle inner wall.

Since the tissue sample is blocked, the operation necessary for separating the sample distal end from the encircling tissue is easier and less traumatic for the patient, as a simple needle rotation is sufficient, without giving the needle oscillatory movements, particularly traumatic for the patient. Furthermore, since the tissue sample is blocked inside the needle, the sample cannot be damaged and cannot protrude from the needle, when the needle is extracted from the patient's body.

The blocking element is generally a very thin, curved blade having the shape of a sector of cylindrical surface. This curved blade has the drawback that it may be very easily damaged, simultaneously damaging the sample, if, during the insertion thereof, the curved blade is blocked against the proximal end of the sample. Therefore, this requires a significant manual skill of the operator carrying out the biopsy. Furthermore, in order that the blocking element may perform its function, it is necessary that the distal end of the needle is tapered, which involves an increase in needle production costs.

Furthermore, from prior art, needles are known of the so-called "guillotine" type, suitable for making biopsies on soft tissues, such as, for example, the hepatic, renal, pulmonary tissue, etc. These needles consist of a substantially cylindrical mandrel, near whose tip a seat is made—for example obtained by a flattened portion made along a mandrel section—suitable for receiving the sample to be collected, and of a hollow needle with a cutting tip, externally slidably coupled with said mandrel. The seat has dimensions such as to receive a tissue sample of sufficient size for the histologic tests to be carried out thereon.

For carrying out the biopsy, the tool is inserted into the patient's body, the mandrel being retracted inside the hollow needle so that only the tip protrudes from the needle. When the mandrel tip has reached the area of the patient's body from which the sample has to be collected, the mandrel is caused to protrude from the needle through axial sliding between the needle and the mandrel. Thus, a tissue portion encircling the mandrel enters the seat obtained on said mandrel. The hollow needle is then moved until it covers said seat, so that the cutting tip of the hollow needle, behaving like a guillotine, separates from the encircling tissue the tissue portion penetrated into said seat.

These needles have the drawback that the tissue amount penetrating into said seat is not always sufficient for a biopsy test, which implies that tissue sample collecting has to be frequently repeated, with consequent trouble for the patient.

The present invention intends to provide a device for transcutaneous biopsy of either rigid or soft tissues, that is simple and easy to be used, that does not involve the above mentioned drawbacks, that is of reasonable cost and allows the patient suffering during the biopsy execution to be minimised. According to the present invention, a device is provided for transcutaneous biopsy of tissues, comprising needle means provided with handle at a proximal end thereof and with cutting edge at a distal end thereof, a mandrel that may be inserted into said needle means, said needle means having a substantially constant diameter, characterised in that it comprises blocking means suitable for blocking a tissue sample inside said needle means, said blocking means being slidably coupled inside said needle means.

The device according to the invention allows a tissue sample to be simply and reliably blocked inside the needle means, without requiring a tapered distal end of the needle means, or a seat for the tissue sample, to be provided. Furthermore, the blocking means is coupled with the needle means so as to avoid the risk that the blocking means may be damaged, if it is blocked against the tissue sample, particularly when a sample of rigid tissue, such as osteomedullary tissue, has to be collected.

The invention may be better understood and carried out with reference to the following description, made for purely exemplifying and not restrictive purpose, and to the attached drawings, wherein.

Figure 1:
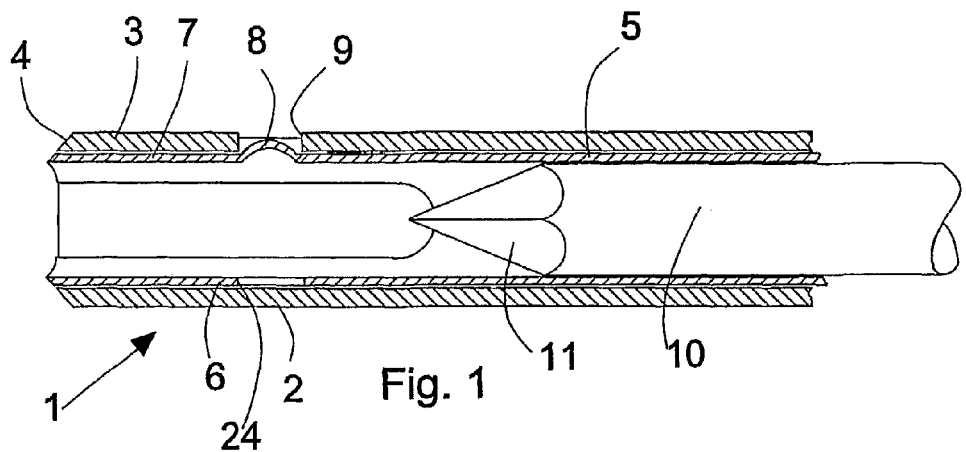
FIG. 1 is a longitudinal section of a first version of a device according to the invention, in a first operating condition.

In FIG. 1, a device according to the invention is indicated with 1, comprising needle means consisting of a cylindrical hollow body 2 provided, at the proximal end thereof, with an operating handle, not shown and removable from the cylindrical hollow body 2. The cylindrical hollow body 2 has a substantially constant diameter and is provided with a non tapered distal end 3 and with a cutting edge 4, the distal end 3 being suitable for penetrating into the patient's body and into the tissue from which a sample has to be collected.

Inside the cylindrical hollow body 2, blocking means 5, 6, 7 is slidably coupled, consisting, for example, of a further cylindrical hollow body 5 ending, at a distal end thereof, with a first elastic lamina 6 and a second elastic lamina 7 facing said first lamina 6, said laminae having the form of a sector of a cylindrical surface. At least one of said laminae 6, 7, for example the second lamina 7, is provided with a protrusion 8 extending towards the outside of the hollow cylinder and suitable for being inserted into an opening 9 made in the wall of the hollow cylinder 2. The other lamina, i.e. the first lamina 6, is provided with a hole 16 positioned in front of said bulge 8. When the blocking means 5, 6, 7 is produced, the hole 16 is used for introducing a punch suitable for making the bulge 8 in the second lamina 7.

Figure 2:
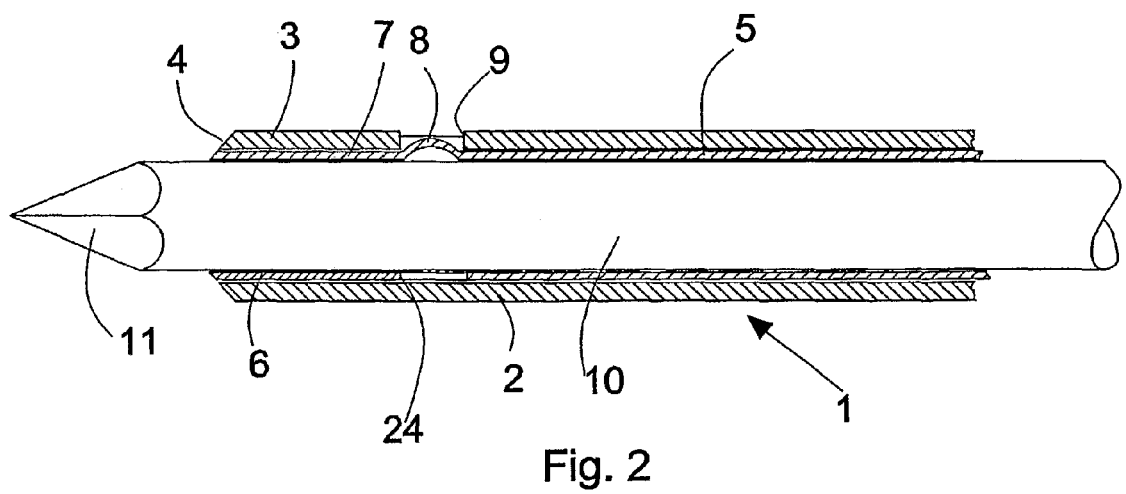
FIG. 2 is a section like FIG. 1, with the device in a second operating condition.
Figure 3:
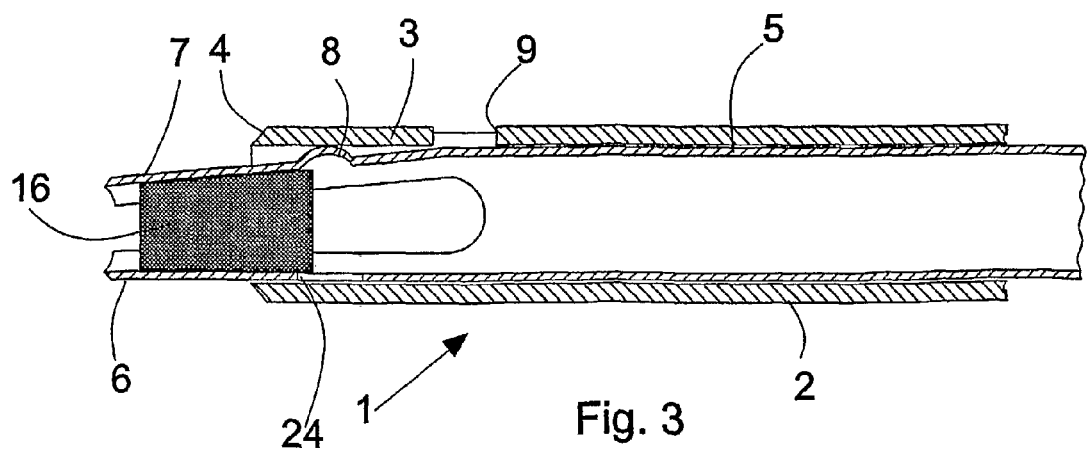
FIG. 3 is a section like FIG. 1, with the device in a third operating condition.

The further cylindrical hollow body 5 is slidable inside the needle 2 between a first position, shown in FIGS. 1 and 2, wherein the distal end of the laminae 6 and 7 is substantially aligned with the distal end 3 of the needle 2 and the bulge 8 is inserted into the slot 9, and a second position, shown in FIG. 3, wherein the distal end of the laminae 6 and 7 protrudes from the distal end 4 of the needle 2, the bulge 8 is completely inside the needle 2 and the second lamina 7 is deflected towards the axis of the needle 2.

The device 1 is completed by a mandrel 10, provided with a penetrating tip 11 and which can be slidably inserted into the further cylindrical hollow body 5, for making the device 1 easier to be inserted into a patient's body.

The device 1 may be provided with sheath means, not shown, that may be caused to slide on the external surface of the needle means 2 for covering the slot 9, so as to prevent the edges of the slot from blocking the needle means 2 during the insertion of said needle means 2 into the patient's body.

The device 1 according to the invention works as explained below: first of all the further cylindrical hollow body 5 is positioned inside the needle 2 in said first position, with the bulge 8 of the lamina 7 inserted into the slot 9 of the needle 2, so that the distal ends of the laminae 6 and 7 are substantially aligned with the distal end 3 of the hollow cylinder 2. The mandrel 10 is then inserted into the further cylindrical hollow body 5 until the tip 11 of the mandrel 10 protrudes from the distal end of the device 1. At this point the device 1 is introduced into the patient's body, and it is pushed until the distal end of the device 1 reaches the area from which the tissue sample has to be collected. In this phase, the penetration of the device 1 is aided by the mandrel 10. After the desired position has been reached, the mandrel 10 (FIG. 2) is withdrawn and the device 1 is further advanced until a sample 16 of tissue to be collected is incorporated between the two laminae 6 and 7. Subsequently, the further cylindrical hollow body 5 is caused to slide in the direction of the distal end 3 of the device 1, so that the distal end of the laminae 6 and 7 protrudes from the distal end 3 of the needle 2. During this operation, the bulge 8 of the lamina 7 leaves the slot 9 and is pushed towards the inside of the needle 2 by the lateral wall of said needle, bending the second lamina 7 towards the axis of the needle 2. The second lamina 7 thus applies a pressure on the sample 16 of tissue, blocking the sample of tissue between the second lamina 7 and the first lamina 6. The device may then be rotated around the axis of the needle 2 for producing the separation of the distal end of the sample 16 of tissue from the encircling tissue and then the device 1 may be retracted from the patient's body, with the assurance that the sample 16 of tissue is blocked between the laminae 6 and 7 and can not protrude from the device, while said device is extracted from the patient's body.

Figure 4:
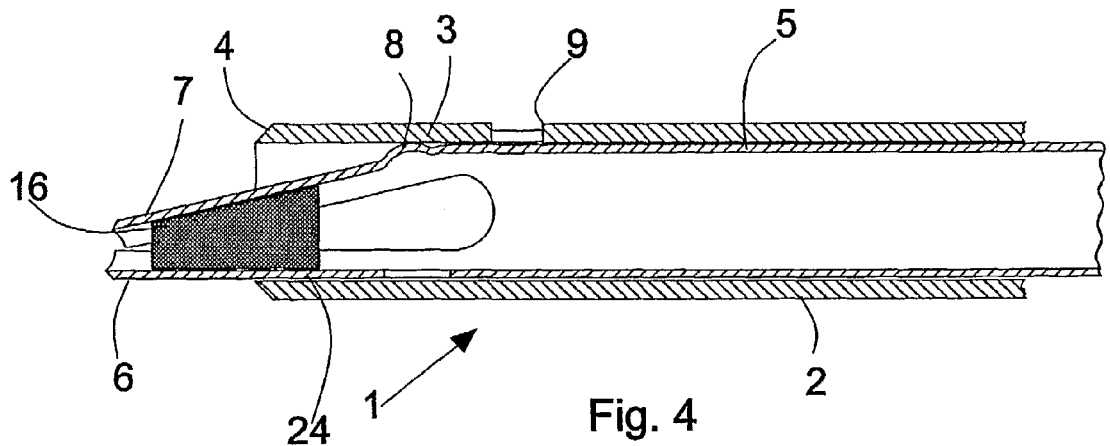
FIG. 4 is a section like FIG. 3, referring to an embodiment of said first version of the device according to the invention, particularly suitable for biopsies in soft tissues.

In FIG. 4 a different embodiment of the device shown in FIGS. 1 to 3 is shown, said different embodiment being particularly suitable for biopsies in soft tissues. In this embodiment, the bulge 8 of the lamina 7 and the slot 9 of the hollow needle 2 are dimensioned and positioned so that, when the further cylindrical hollow body 5 is advanced towards said distal end 3, the second lamina 7 undergoes a greater deflection, until said second lamina 7 substantially contacts the second lamina 6, completing the separation of the sample 16 of tissue from the encircling tissue, and furthermore blocking said tissue 16 between said second lamina 7 and the first lamina 6.

Figure 5:
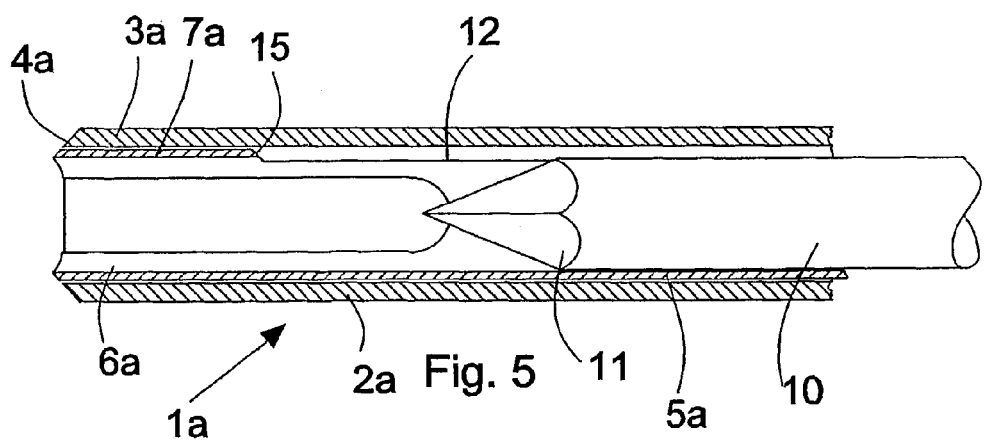
FIG. 5 is a longitudinal section of a second version of a device according to the invention in a first operating condition.
Figure 6:
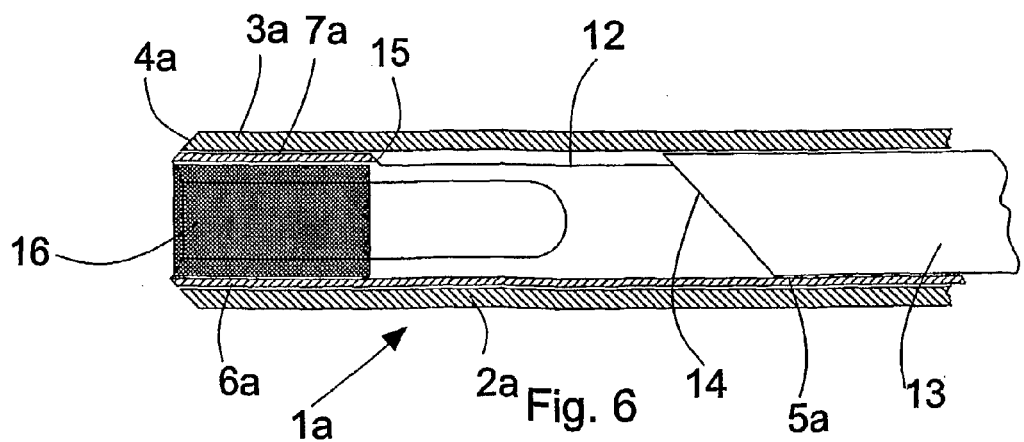
FIG. 6 is a longitudinal section like FIG. 4, but with the device according to the invention in a second operating condition.
Figure 7:
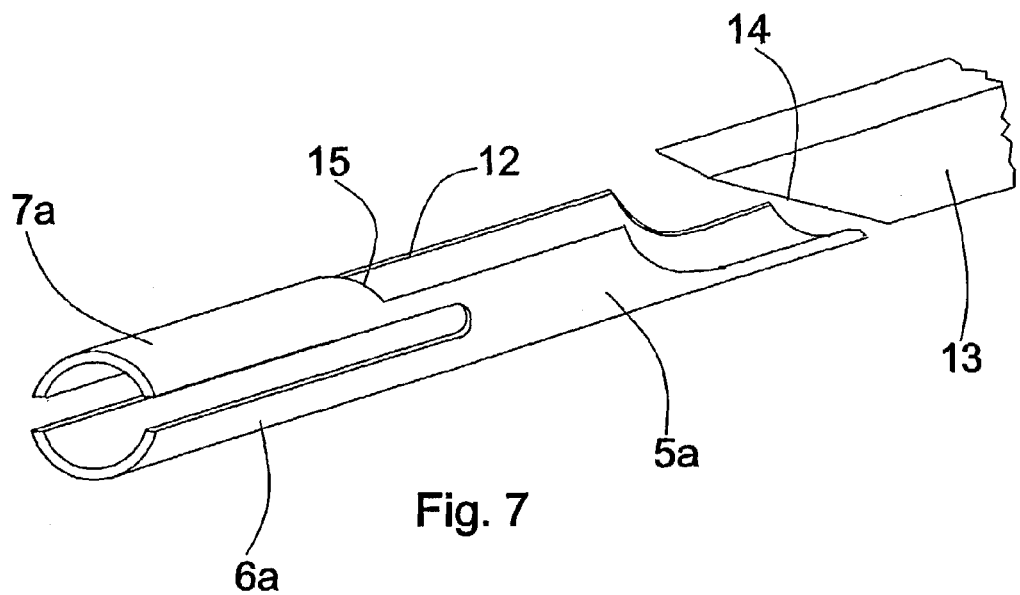
FIG. 7 is a perspective view of a detail of the device of FIG. 4.

In FIGS. 5 to 7, a second version is shown of a device according to the invention.

The device 1a comprises needle means consisting of a first cylindrical hollow body 2a having a substantially constant diameter and provided with a non tapered distal end 3a, having a cutting edge 4a.

Blocking means 5a, 6a, 7a is slidably coupled inside the cylindrical hollow body 2a, the blocking means 5a, 6a, 7a comprising a further cylindrical hollow body 5a ending at a distal end thereof with a first elastic lamina 6a and a second elastic lamina 7a facing said first lamina 6a, said laminae having the form of a sector of cylindrical surface. In the further cylindrical hollow body 5a a slot 12 is made, extending from the proximal end of the further cylindrical hollow body 5a up to the initial section of the lamina 7a. The device 1a is provided with pusher means 13 which may be inserted into the further cylindrical hollow body 5a and which is provided with wedge-shaped end 14, shaped so as to slidably couple into the slot 12.

Figure 8:
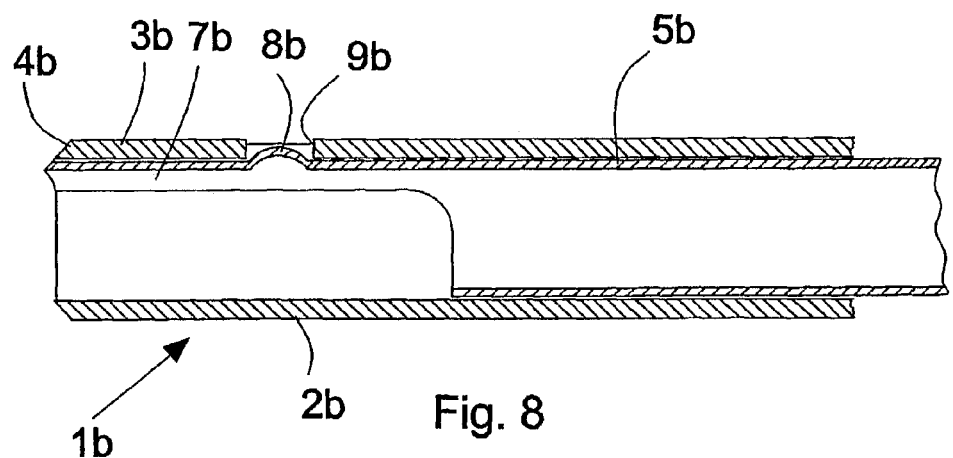
FIG. 8 is a longitudinal section of a third version of a device according to the invention in a first operating condition.
Figure 9:
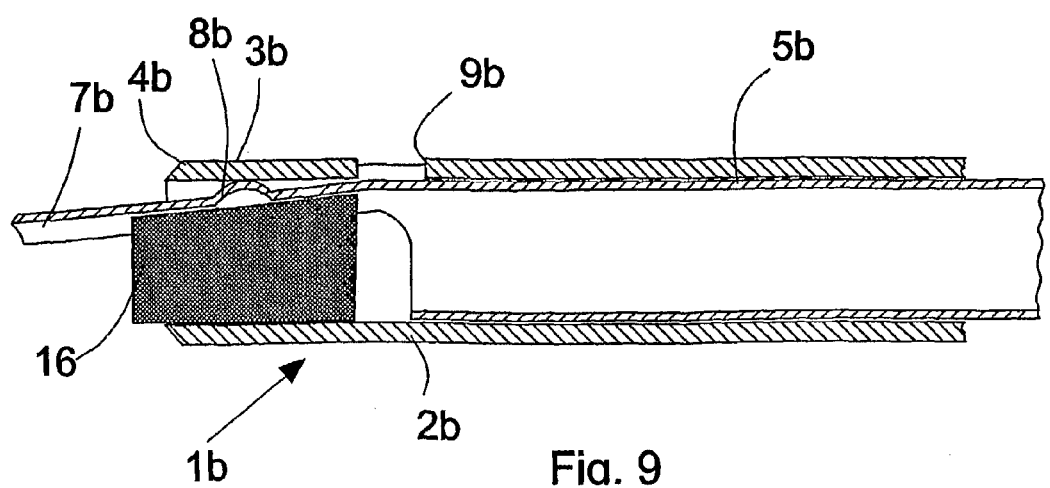
FIG. 9 is a longitudinal section like FIG. 8, but with the device according to the invention in a second operating condition.

If the pusher means 13 is inserted into the further cylindrical hollow body 5a, when the wedge-shaped end 14 of said pusher means 13 contacts the end 15 of the slot 12, said end 14 bends the lamina 7a towards the axis of the needle 2a, i.e. towards the other lamina 6a, thus entrapping through pressure a sample 16 of tissue inserted between said laminae. In FIGS. 8 and 9 a third version of a device 1b according to the invention is shown.

The device 1b comprises needle means comprising a cylindrical hollow body 2b having a substantially constant diameter and provided with a non tapered distal end 3b, with cutting edge 4b.

The cylindrical hollow body 2b is provided, at a distal end 3b thereof, with a pair of bulges 17, 18, mutually diametrically facing, extending towards the inside of the cylindrical hollow body 2b.

This third version differs from the first version shown in FIGS. 1 to 3 in that the blocking means consists of a further cylindrical hollow body 5b ending, at the distal end thereof, with a single elastic lamina 7b having the form of a sector of cylindrical surface. The lamina 7b is provided with a bulge 8b extending towards the outside of the further hollow cylinder 5b and suitable for being inserted into an opening 9b made in the wall of the hollow cylinder 2b. The third version 1b of the device according to the invention works absolutely similarly to the first version 1 shown in FIGS. 1 to 3. In particular, when the further cylindrical hollow body 5b is caused to slide in direction of the distal end of the device 1b, the bulge 8b of the lamina 7b leaves the slot 9b and is pushed towards the inside of the needle 2b by the lateral wall of said needle, bending the lamina 7b towards the axis of the needle 2b. The lamina 7b thus applies a pressure on the sample of tissue 16, blocking the sample of tissue 16 between said lamina 7b and the opposite wall of the cylindrical body 2b.

Figure 10:
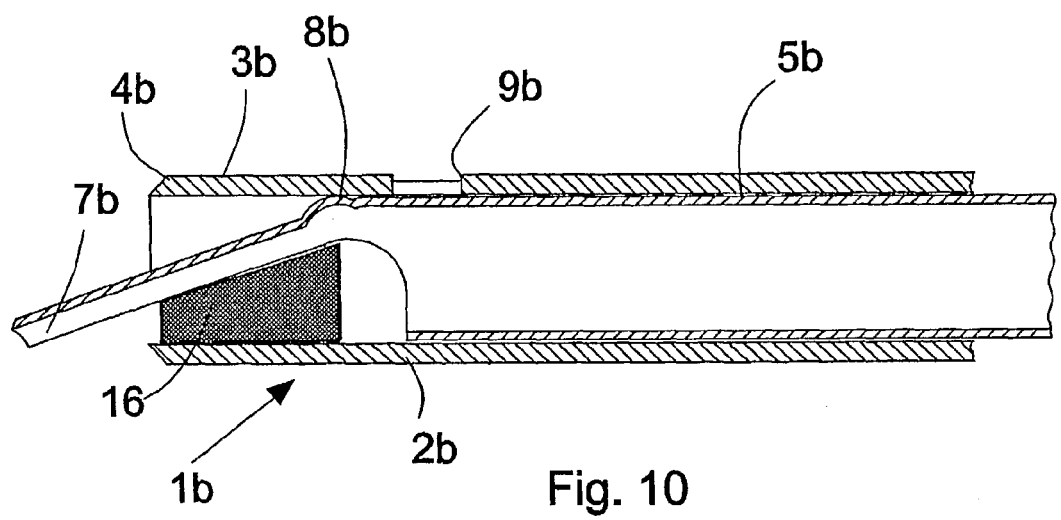
FIG. 10 is a longitudinal section like FIG. 9, referring to an embodiment of said third version of the device according to the invention, particularly suitable for biopsies in soft tissues.

In FIG. 10 a different embodiment of the device shown in FIGS. 8 and 9 is shown, said different embodiment being particularly suitable for biopsies in soft tissues. In this embodiment the bulge 8b of the lamina 7b and the slot 9b of the hollow needle 2b are dimensioned and positioned so that, when the further cylindrical hollow body 5b is advanced in direction of said distal end 3b, the second lamina 7b undergoes a greater deflection, until said second lamina 7b substantially contacts the first lamina 6b, completing the separation of the sample of tissue 16 from the encircling tissue, and blocking furthermore the sample of tissue 16 between said second lamina 7b and the first lamina 6b.

Figure 11:
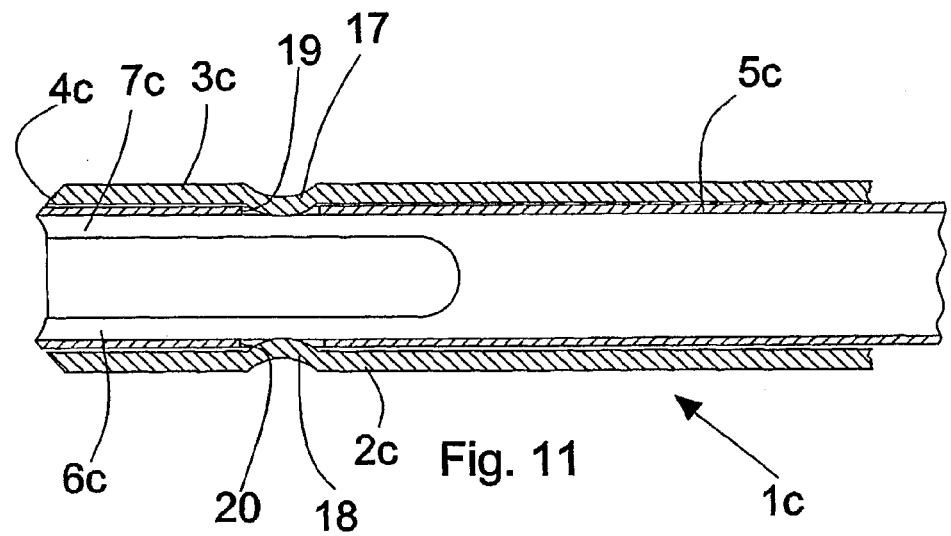
FIG. 11 is a longitudinal section of a fourth version of a device according to the invention in a first operating condition.
Figure 12:
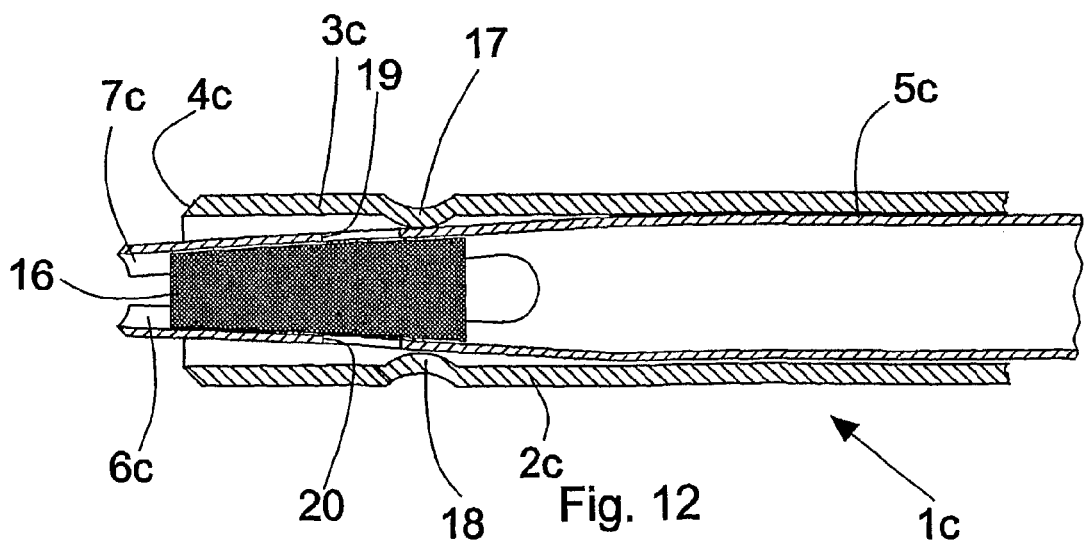
FIG. 12 is a longitudinal section like FIG. 11, but with the device according to the invention in a second operating condition.

In FIGS. 11 and 12 a fourth version of a device 1c for biopsy according to the invention is shown.

In this fourth version, the cylindrical hollow body 2c is provided, at a distal end 3c thereof, with a pair of bulges 17, 18, mutually diametrically facing, extending towards the inside of the cylindrical hollow body 2c.

The blocking means 5c, 6c, 7c comprises a further cylindrical hollow body 5c ending, at a distal end thereof, with a pair of elastic laminae 6c, 7c, mutually facing and having the shape of a sector of cylindrical surface. Each elastic lamina 6c, 7c is provided with a respective slot 20, 19, suitable for coupling with the respective bulge 18, 17 of the further cylindrical hollow body 5c.

The fourth version 1c of the device according to the invention works similarly to the first version 1, shown in FIGS. 1 to 3: first of all the hollow further cylindrical body 5c is positioned inside the cylindrical hollow body 2c, in a first position in which the bulges 17 and 18 of the cylindrical hollow body 2c are inserted into the slots 19, 20 of the laminae 7c and 6c, respectively, so that the distal ends of the laminae 6c and 7c are substantially aligned with the distal end 3c of the cylindrical hollow body 2c. The device 1c is then inserted into the patient's body, with the aid of the mandrel 10, as previously described, until the desired position for collecting a sample of tissue is reached and said sample is incorporated between the two laminae 6c and 7c. The further cylindrical hollow body 5c is then caused to slide in direction of the distal end 3c of the cylindrical hollow body 2c, so that the distal end of the laminae 6c and 7c protrudes form said distal end 3c. In this operation, the bulges 17 and 18 of the cylindrical hollow body 2c leave the slots 19, 20 of the laminae 7c, 6c and push said laminae towards the inside of the cylindrical hollow body 2c, bending said laminae towards the axis of said cylindrical hollow body 2c. The laminae 6c, 7c thus apply a pressure on the sample of tissue 16, blocking said sample of tissue between said laminae 6c, 7c, so as to allow the sample of tissue to be separated from the encircling tissue and to be subsequently extracted from the patient's body.

Figure 13:
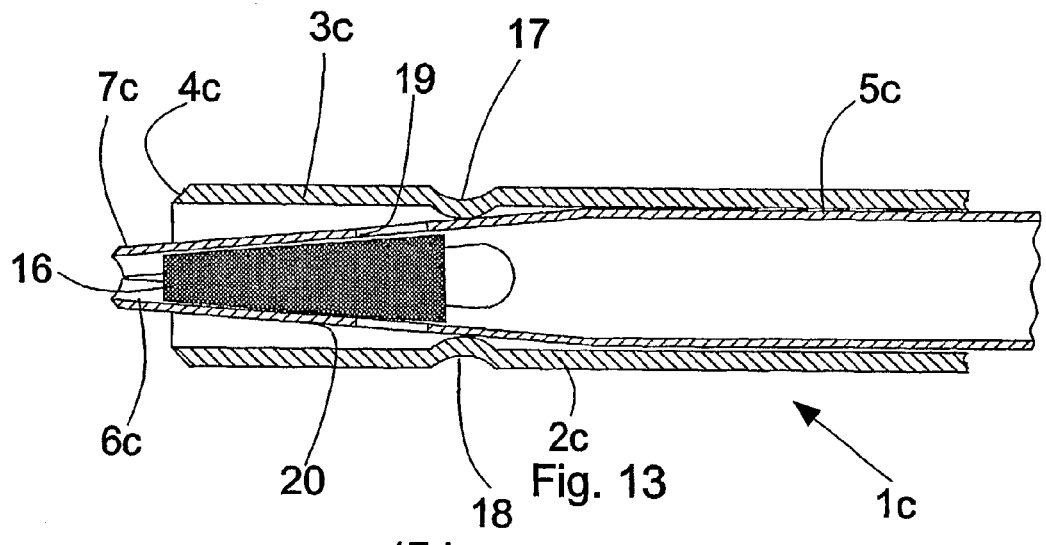
FIG. 13 is a longitudinal section like FIG. 12, referring to an embodiment of said fourth version of the device according to the invention, particularly suitable for biopsies in soft tissues.

In FIG. 13 a different embodiment of the device shown in FIGS. 11 and 12 is shown, said different embodiment being particularly suitable for biopsies in soft tissues. In this embodiment, the bulges 17 and 18 of the cylindrical hollow body 2c and the slots 19, 20 of the laminae 7c and 6c, respectively, are dimensioned and positioned so that, when the further cylindrical hollow body 5c is advanced in direction of said distal end 3c, the first lamina 6c and the second lamina 7c undergo a greater deflection, until they substantially mutually contact, completing the separation of the sample 16 of tissue from the encircling tissue, and blocking furthermore the sample of tissue 16 between said laminae.

Figure 14:
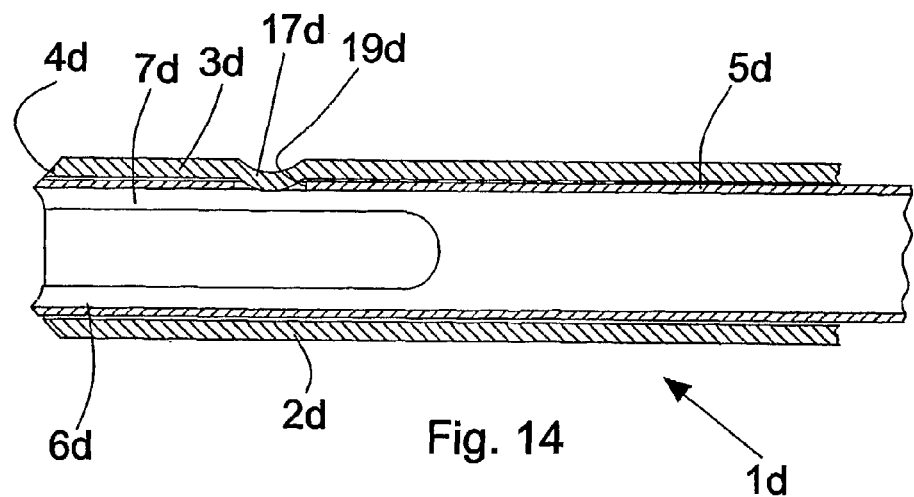
FIG. 14 is a longitudinal section of a fifth version of a device according to the invention in a first operating condition.
Figure 15:
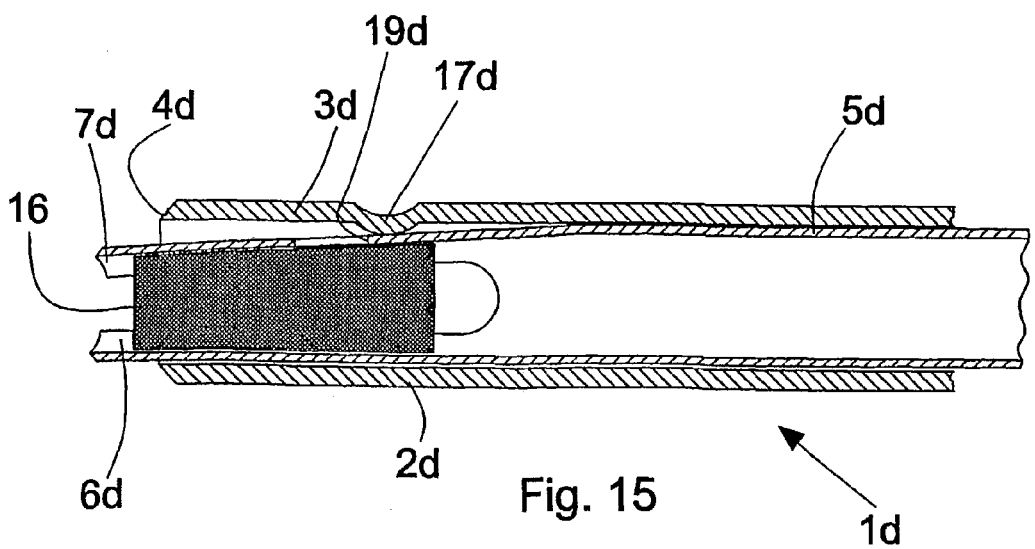
FIG. 15 is a longitudinal section like FIG. 14, but with the device according to the invention in a second operating condition.

In FIGS. 14 and 15 a fifth version is shown of a device 1d for biopsy according to the invention.

In this fifth version, the cylindrical hollow body 2d is provided, at a distal end 3d thereof, with a bulge 17d extending towards the inside of the cylindrical hollow body 2d.

The blocking means 5d, 6d, 7d comprises a hollow further cylindrical body 5d ending, at a distal end thereof, with a pair of elastic laminae 6d, 7d, mutually facing and having the shape of a sector of cylindrical surface. A lamina 7d of said elastic laminae 6d, 7d is provided with a slot 19d, suitable for coupling with the bulge 17d of the further cylindrical hollow body 5d.

The fifth version 1d of the device according to the invention works similarly to the fourth version 1c, shown in FIGS. 9 and 10: first of all the further cylindrical hollow body 5d is positioned inside the cylindrical hollow body 2d, in a first position in which the bulge 17d of the cylindrical hollow body 2d is inserted into the slot 19d of the lamina 7d, so that the distal ends of the laminae 6d and 7d are substantially aligned with the distal end 3d of the cylindrical hollow body 2d. The device 1d is then inserted into the patient's body, with the aid of the mandrel 10, as previously described, until the desired position for collecting a sample of tissue is reached and said sample is incorporated between the two laminae 6d and 7d. The further cylindrical hollow body 5d is then caused to slide in direction of the distal end 3d of the cylindrical hollow body 2d, so that the distal end of the laminae 6d and 7d protrudes from said distal end 3d. In this operation, the bulge 17d of the cylindrical hollow body 2d leaves the slot 19d of the lamina 7d and pushes said lamina 7d towards the inside of the cylindrical hollow body 2d, bending said lamina 7d towards the axis of the cylindrical hollow body 2d. The lamina 7d thus applies a pressure on the sample of tissue 16, blocking the sample of tissue 16 between said lamina 7d and the lamina 6d, so as to allow the sample of tissue 16 to be separated from the encircling tissue and to be subsequently extracted from the patient's body.

Figure 16:
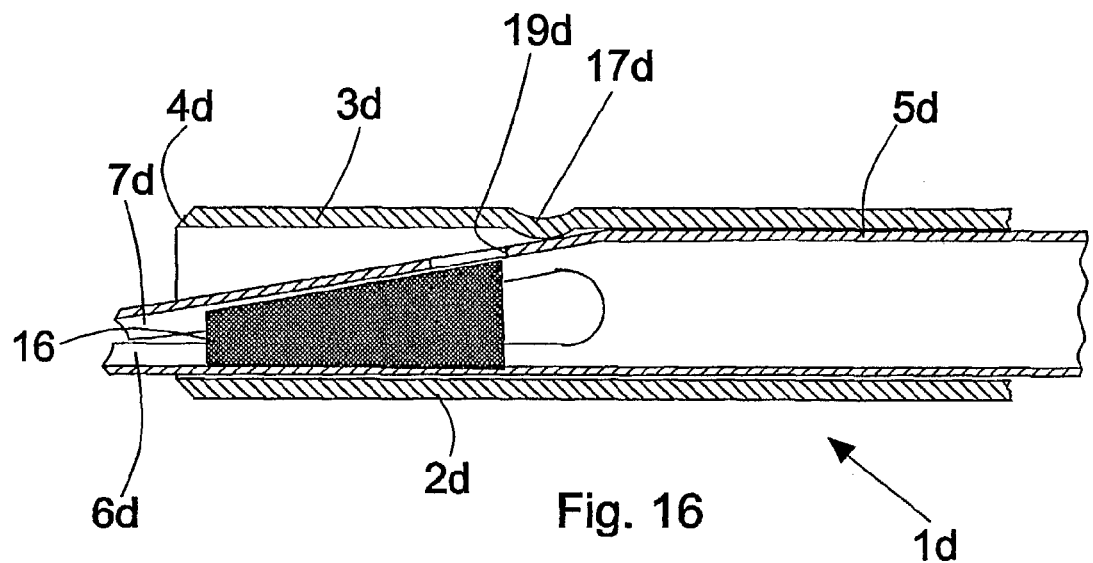
FIG. 16 is a longitudinal section like FIG. 15, referring to an embodiment of said fourth version of the device according to the invention, particularly suitable for biopsies in soft tissues.

In FIG. 16 a different embodiment of the device shown in FIGS. 14 and 15 is shown, said different embodiment being particularly suitable for biopsies in soft tissues. In this embodiment, the bulge 17d of the cylindrical hollow body 2d and the slot 19d of the second lamina 7d are dimensioned and positioned so that, when the further cylindrical hollow body 5d is advanced in direction of said distal end 3d, the second lamina 7d undergoes a greater deflection, until it substantially contacts the first lamina 6d, completing the separation of the simple of tissue 16 from the encircling tissue, and furthermore blocking the sample of tissue 16 between said second lamina 7d and the first lamina 6d.

Figure 17:
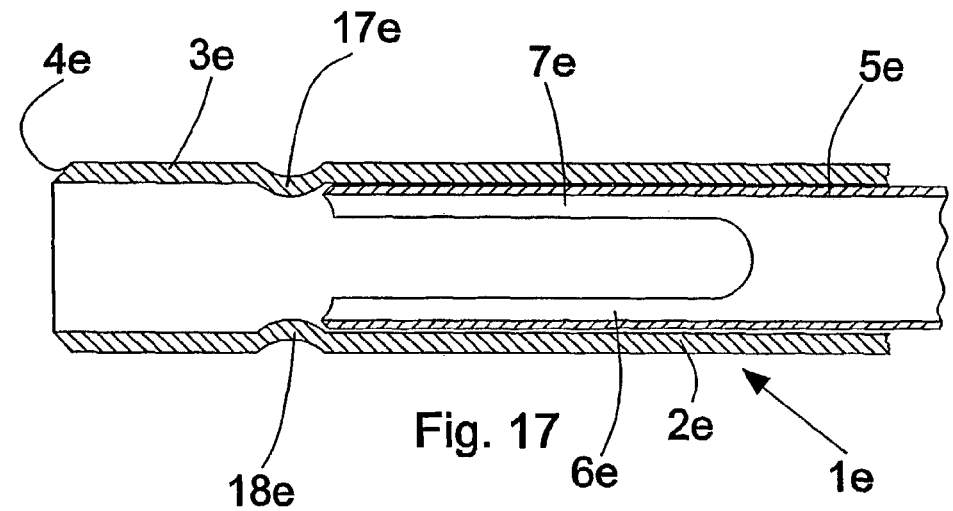
FIG. 17 is a longitudinal section of a sixth version of a device according to the invention in a first operating condition.
Figure 18:
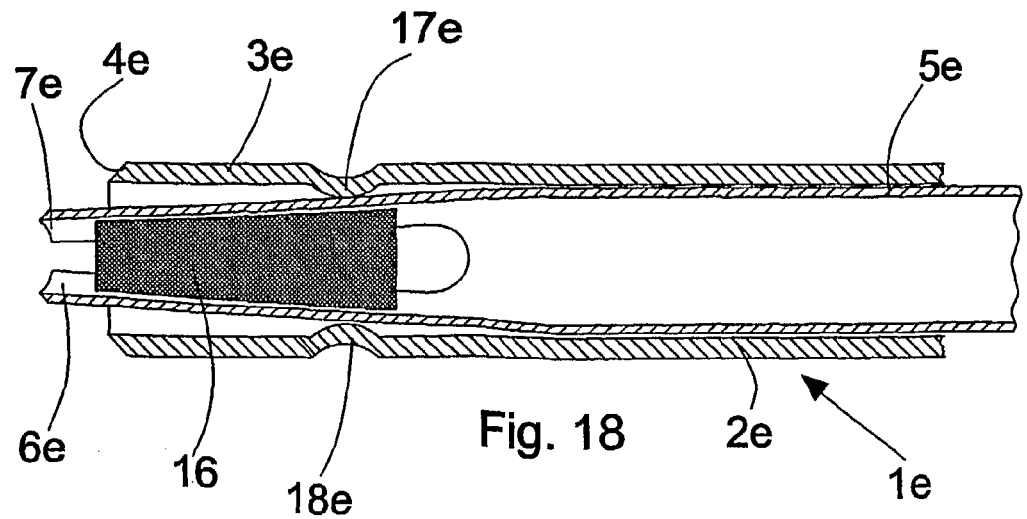
FIG. 18 is a longitudinal section like FIG. 17, but with the device according to the invention in a second operating condition.

In FIGS. 17 and 18 a sixth version of a device 1e for biopsy according to the invention is shown.

In this sixth version, the cylindrical hollow body 2e is provided, at a distal end 3e thereof, with a pair of bulges 17e, 18e, diametrically facing, extending towards the inside of the cylindrical hollow body 2e.

The blocking means 5e, 6e, 7e comprises a further cylindrical hollow body 5e ending, at a distal end thereof, with a pair of elastic laminae 6e, 7e, mutually facing and having the shape of a sector of cylindrical surface.

The sixth version 1e of the device according to the invention works as described below: first of all the further cylindrical hollow body 5e is positioned inside the cylindrical hollow body 2e, in a first position in which the distal ends of the laminae 6e, 7e are slightly back positioned with respect to the bulges 17e, 18e of the cylindrical hollow body 2e, so that the laminae 6e and 7e are substantially mutually parallel and parallel to the longitudinal axis of the cylindrical hollow body 2e. The device 1e is then inserted into the patient's body, with the aid of the mandrel 10, as previously described, until the desired position for collecting a sample of tissue is reached and said sample is incorporated into the distal end 3e of the cylindrical hollow body 2e. Then, the further cylindrical hollow body 5e is caused to slide in direction of the distal end 3e of the cylindrical hollow body 2e, so that the distal end of the laminae 6e and 7e protrudes from said distal end 3e. In this operation, the bulges 17e, 18e of the cylindrical hollow body 2e push the laminae 6e, 7e towards the inside of the cylindrical hollow body 2e, bending the laminae 6e, 7e towards the axis of the cylindrical hollow body 2e. The laminae 6e, 7e are thus inserted between the inner wall of the cylindrical hollow body 2e and the sample of tissue 16, applying a pressure on the sample of tissue 16 and blocking said sample of tissue 16 between said laminae 6e, 7e, so as to allow the sample of tissue 16 to be separated from the encircling tissue and to be subsequently extracted from the patient's body.

Figure 19:
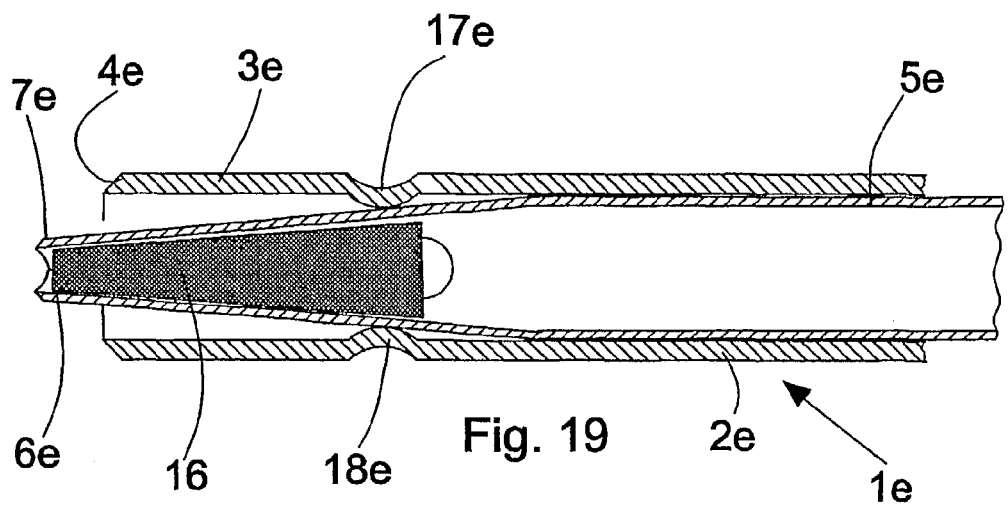
FIG. 19 is a longitudinal section like FIG. 8, referring to an embodiment of said sixth version of the device according to the invention, particularly suitable for biopsies in soft tissues.

In FIG. 19 a different embodiment of the device shown in FIGS. 17 and 18 is shown, said different device being particularly suitable for biopsies in soft tissues. In this embodiment the bulges 17e and 18e of the cylindrical hollow body 2c are dimensioned and positioned so that, when the further cylindrical hollow body 5e is advanced in direction of said distal end 33, the first lamina 6e and the second lamina 7e undergo a greater deflection, until they substantially mutually contact, completing the separation of the sample of tissue 16 from the encircling tissue, and furthermore blocking said sample of tissue between said laminae 6e, 7e.

Figure 20:
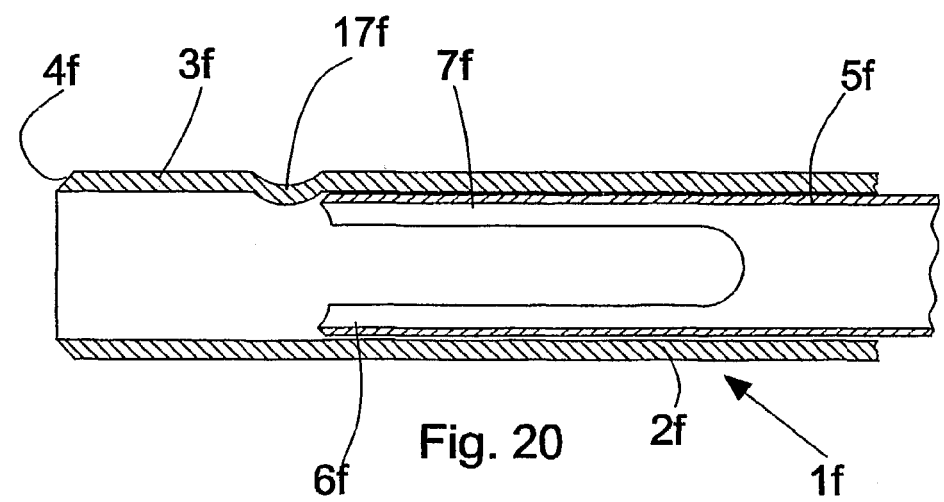
FIG. 20 is a longitudinal section of a seventh version of a device according to the invention in a first operating condition.
Figure 21:
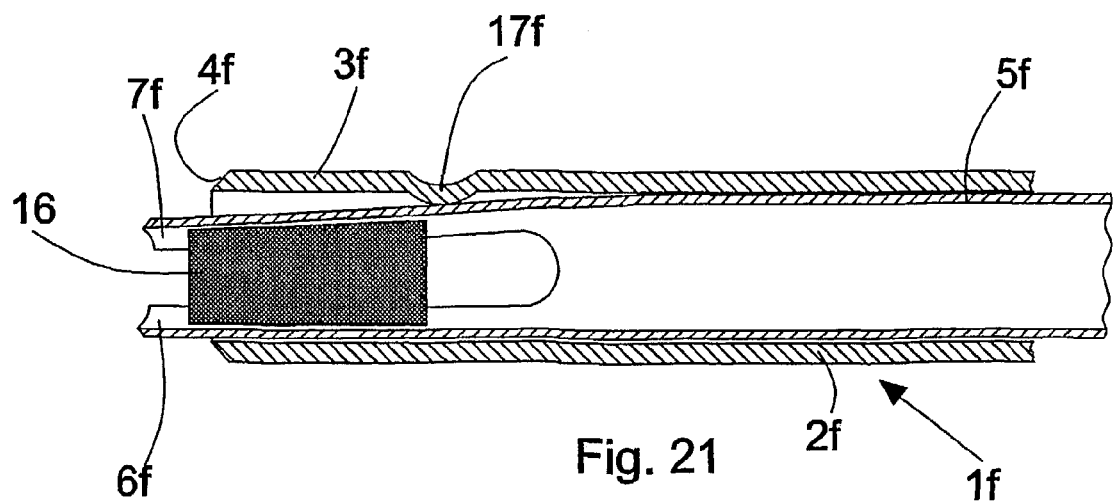
FIG. 21 is a longitudinal section like FIG. 20, but with the device according to the invention in a second operating condition.

In FIGS. 20 and 21 a seventh version of a device 1f for biopsy according to the invention is shown.

In this seventh version, the cylindrical hollow body 2f is provided, at a distal end 3f thereof, with a bulge 17f, extending towards the inside of the cylindrical hollow body 2f.

The blocking means 5f, 6f, 7f comprises a further cylindrical hollow body 5f ending, at a distal end thereof, with a pair of elastic laminae 6f, 7f, mutually facing and having the shape of a sector of cylindrical surface.

The seventh version 1f of the device according to the invention works as described below: first of all the further cylindrical hollow body 5f is positioned inside the cylindrical hollow body 2f, in a first position in which the distal end of the lamina 7f is slightly back positioned with respect to the bulge 17f of the cylindrical hollow body 2f, so that the laminae 6e and 7f are substantially mutually parallel and parallel to the longitudinal axis of the cylindrical hollow body 2f. The device 1e is then inserted into the patient's body, with the aid of the mandrel 10, as previously described, until the desired position for collecting a sample of tissue is reached and said tissue is incorporated into the distal end 3f of the cylindrical hollow body 2f. Then, the further cylindrical hollow body 5f is caused to slide in direction of the distal end 3f of the cylindrical hollow body 2f, so that the distal end of the laminae 6f and 7f protrudes from said distal end 3f. In this operation, the bulge 17f of the cylindrical hollow body 2f pushes the lamina 7f towards the inside of the cylindrical hollow body 2f, bending the lamina 7f towards the axis of the cylindrical hollow body 2f. The laminae 6f, 7f are thus inserted between the inner wall of the cylindrical hollow body 2f and the sample of tissue 16, and the lamina 7f applies a pressure on said sample of tissue 16, blocking said sample of tissue 16 between said lamina 7f and the lamina 6f, so as to allow the sample of tissue 16 to be separated from the encircling tissue and to be subsequently extracted from the patient's body.

Figure 22:
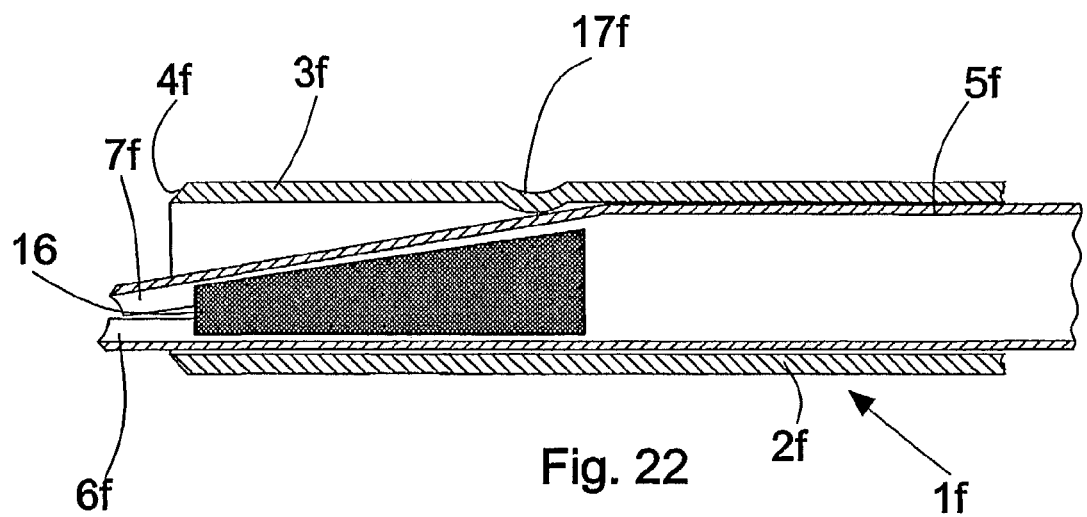
FIG. 22 is a longitudinal section like FIG. 21 relative to a variant of said seventh version of the device according to the invention, particularly suitable for biopsies in soft tissues.

In FIG. 22 a different embodiment of the device shown in FIGS. 20 and 21 is shown, said different embodiment being particularly suitable for biopsies in soft tissues. In this embodiment, the bulge 17f of the cylindrical hollow body 2f is dimensioned and positioned so that, when the further cylindrical hollow body 5f is advanced in direction of said distal end 3f, the second lamina 7f undergoes a greater deflection, until it substantially contacts the first lamina 6f, completing the separation of the sample of tissue 16 from the encircling tissue, and furthermore blocking said sample of tissue between said lamina 7f and the first lamina 6f.

Figure 23:
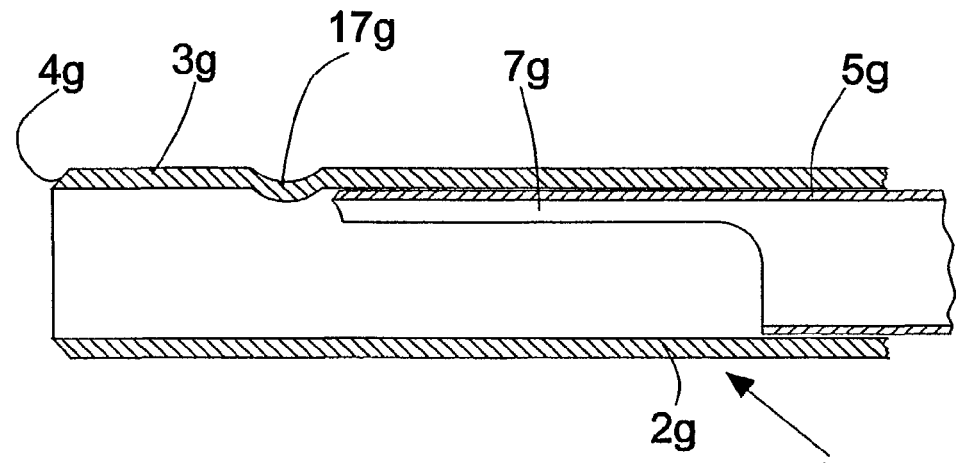
FIG. 23 is a longitudinal section of an eighth version of a device according to the invention in a first operating condition.
Figure 24:
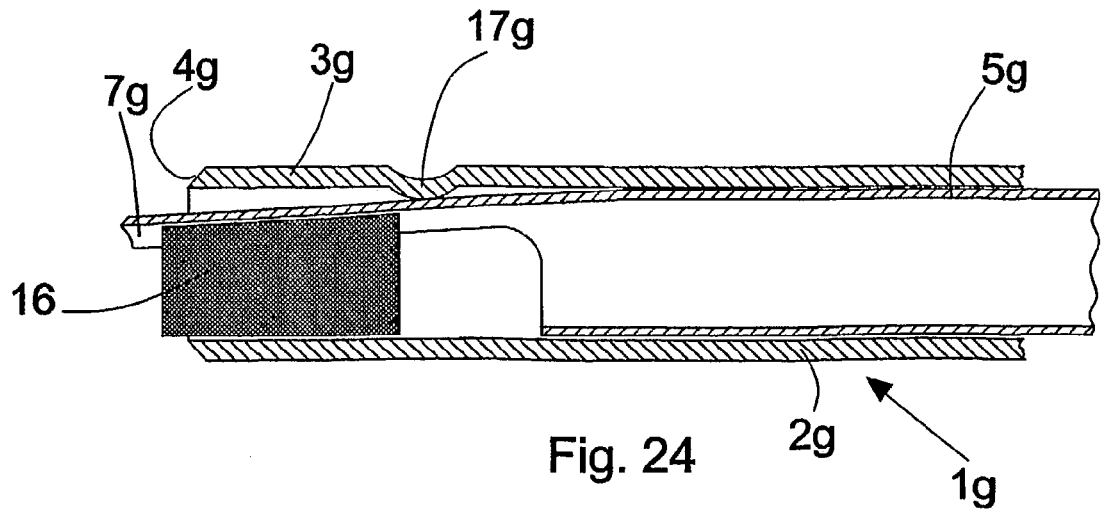
FIG. 24 is a longitudinal section like FIG. 23, but with the device according to the invention in a second operating condition.

In FIGS. 23 and 24 an eighth version of a device 1g for biopsy according to the invention is shown.

In this eighth version, the cylindrical hollow body 2g is provided, at a distal end 3g thereof, with a bulge 17g, extending towards the inside of the cylindrical hollow body 2g.

The blocking means 5g, 6g comprises a further cylindrical hollow body 5g ending, at a distal end thereof, with an elastic lamina 7g, having the shape of a sector of cylindrical surface.

The eighth version 1g of the device according to the invention works as described below: first of all the further cylindrical hollow body 5g is positioned inside the cylindrical hollow body 2g, in a first position in which the distal end of the lamina 7g is slightly back positioned with respect to the bulge 17g of the cylindrical hollow body 2g, so that the lamina 7g is substantially parallel to the longitudinal axis of the cylindrical hollow body 2a. The device 1e is then inserted into the patient's body, with the aid of the mandrel 10, as previously described, until the desired position for collecting a sample of tissue is reached and said sample is incorporated into the distal end 3g of the cylindrical hollow body 2g. The further cylindrical hollow body 5g is then caused to slide in direction of the distal end 3g of the cylindrical hollow body 2g, so that the distal end of the lamina 7g protrudes from said distal end 3g. In this operation, the bulge 17g of the cylindrical hollow body 2g pushes the lamina 7g towards the inside of the cylindrical hollow body 2g, bending the lamina 7g towards the axis of the cylindrical hollow body 2g. Thus, the lamina 7g is inserted between the inner wall of the cylindrical hollow body 2g and the sample of tissue 16 and applies a pressure on said sample of tissue 16, blocking said sample of tissue 16 between said lamina 7g and the facing inner wall of the cylindrical hollow body 2g, so as to allow the sample of tissue to be separated from the encircling tissue and to be subsequently extracted from the patient's body.

Figure 25:
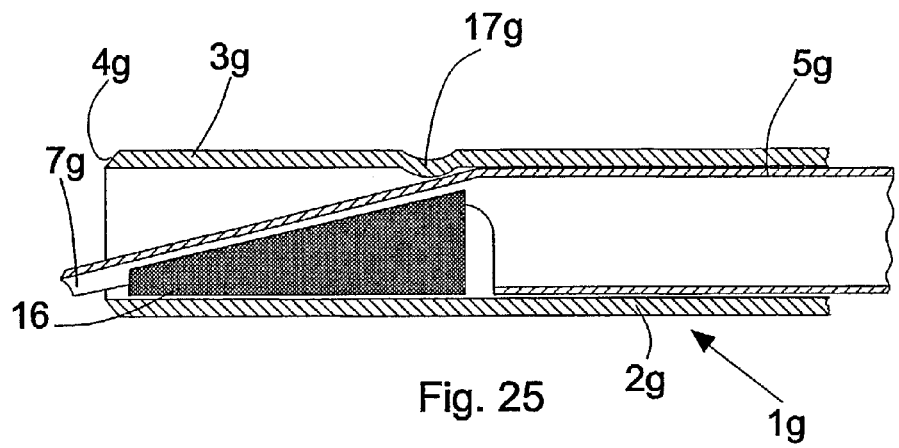
FIG. 25 is a longitudinal section like FIG. 24, referring to an embodiment of said eighth version of the device according to the invention, particularly suitable for biopsies in soft tissues.

In FIG. 25 a different embodiment of the device shown in FIGS. 23 and 24 is shown, said different embodiment being particularly suitable for biopsies in soft tissues. In this embodiment, the bulge 17g of the cylindrical hollow body 2g is dimensioned and positioned so that, when the further cylindrical hollow body 5g is advanced in direction of said distal end 3g, the second lamina 7g undergoes a greater deflection, until said second lamina 7g substantially contacts the first lamina 6g, completing the separation of the sample of tissue 16 from the encircling tissue, and furthermore blocking said sample of tissue 16 between said second lamina 7g and the first lamina 6g.

Figure 26:
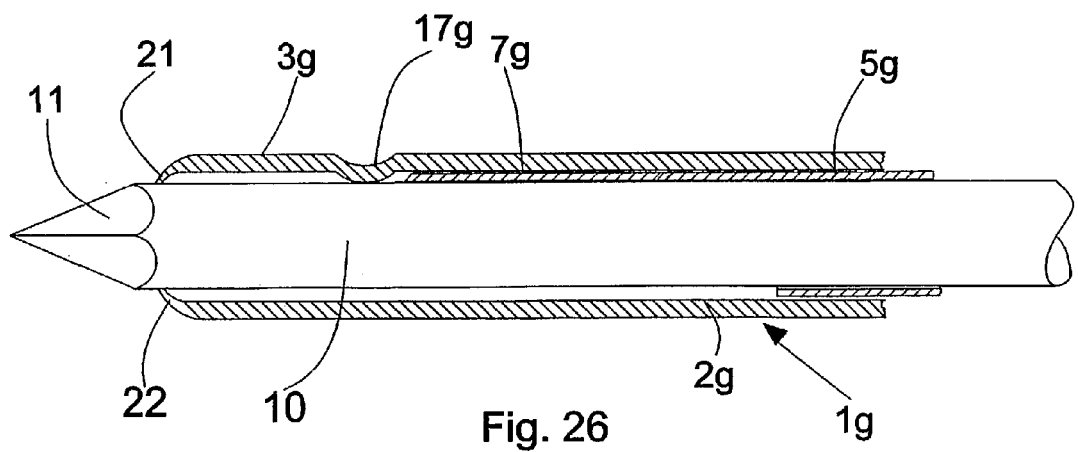
FIG. 26 is a longitudinal section of a further embodiment of the device of FIGS. 23 and 24.

In FIG. 26 a further embodiment of the eighth version 1g of the device for biopsy according to the invention is shown. In this, embodiment, the distal end 3g of the cylindrical hollow body 2g ends with a narrowed portion 21, 22, so dimensioned that the mouthpiece of the cylindrical hollow body 2g, at said distal end 3g, has a diameter substantially corresponding to the inner diameter of the further cylindrical hollow body 5g. This allows the lamina 7g to be more easily inserted between the sample of tissue 16 and the inner wall of the cylindrical hollow body 2g, avoiding any risk of damaging the sample of tissue 16, while the lamina 7g is inserted.

Figure 27:
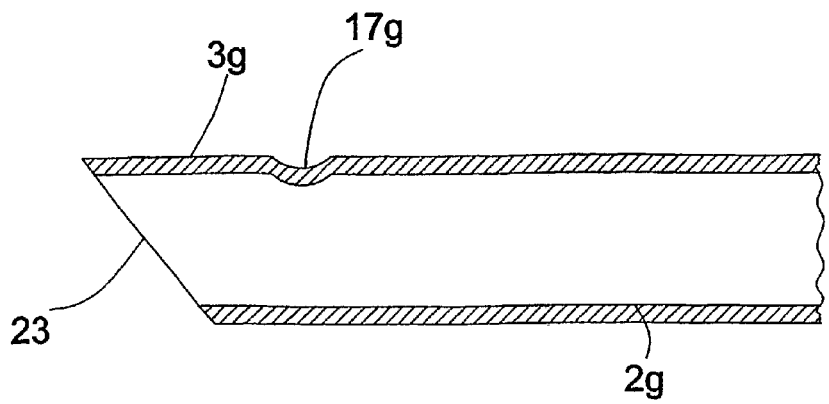
FIG. 27 is a longitudinal section of a detail of a still further embodiment of the device according to the invention.

This embodiment of the device according to the invention may be advantageously adopted even in any of the previously described embodiments, from the fourth one to the seventh one. In FIG. 27 a still further embodiment of the eighth version of the device according to the invention is shown, in which the cylindrical hollow body 2g ends, at a distal end 3g thereof, with a tip 23 having a flute mouthpiece shape. This allows the device according to the invention to be more easily inserted into the patient's body.

The above mentioned shape of the tip of the distal end of the device according to the invention may be advantageously adopted in any of the previously described versions of the device.

It is to be noted that that the distal ends of the elastic laminae 6, 7; 6a, 7a; 7b; 6c, 7c; 6d, 7d; 6e, 7e; 6f, 7f; 7g are advantageously sharp, particularly when the device according to the invention has to be used for collecting samples of soft tissues; this is important in order that said sharp ends, when the elastic laminae are deflected, may complete, as already said, the separation of the sample of tissue 16 from the encircling tissue, making easier the operation of cutting off the sample of tissue.

In the practical embodiment, the materials, the dimensions and the construction details may be different from those indicated, but technically equivalent thereto, without thereby departing from the legal domain of the present invention.

What is claimed is:

1. A device for transcutaneous biopsy of rigid tissues comprising:
    (a) needle means comprising a substantially cylindrical first hollow body comprising a first hollow body distal end, a cutting edge at said first hollow body distal end, and a substantially constant inner diameter; and
    (b) blocking means slidably coupled inside said needle means for blocking a sample of tissue inside said needle means, said blocking means comprising a substantially cylindrical second hollow body slidably coupled inside said needle means and having a second hollow body distal end, said second hollow body ending at said second hollow body distal end with at least one elastic lamina means comprising a first lamina and a second lamina facing said first lamina and having a beginning;
    wherein said second hollow body comprises a longitudinal slot extending from a proximal end of said second hollow body up to about the beginning of said second lamina.

2. Device according to claim 1, wherein said at least one elastic lamina means is shaped as a sector of a cylindrical surface.

3. Device according to claim 1, further comprising pusher means suitable for pushing said second lamina radially towards said first lamina.

4. Device according to claim 3, wherein said pusher means is provided with a wedge-shaped end for engaging into said slot.

5. Device according to claim 1, wherein said first hollow body ends at the first hollow body distal end with a tip having an oblique shape.

6. Device according to claim 1, further comprising mandrel means insertable into said second hollow body.

7. Device according to claim 1, further comprising sheath means slidable on said needle means for covering said slot.

8. A device for transcutaneous biopsy of rigid tissues comprising:
    (a) needle means comprising a substantially cylindrical first hollow body comprising a first hollow body distal end, a mouth and a cutting edge at said distal end, a substantially constant inner diameter, and at least one bulge extending toward an inside portion of said first hollow body; and
    (b) blocking means slidably coupled inside said needle means for blocking a sample of tissue inside said needle means;
    wherein said at least one bulge comprises a pair of mutually facing bulges.

9. Device according to claim 8, wherein said first hollow body ends at the first hollow body distal end with a tip having an oblique shape.

10. A device for transcutaneous biopsy of rigid tissues comprising:
    (a) needle means comprising a distal end, a mouth and a cutting edge at said distal end, and a substantially cylindrical hollow body having a substantially constant inner diameter and at least one bulge extending toward an inside portion of said cylindrical hollow body; and
    (b) blocking means slidably coupled inside said needle means for blocking a sample of tissue inside said needle means, said blocking means comprising at least one elastic lamina means comprising a respective slot for coupling with said at least one bulge.

11. Device according to claim 10, wherein said at least one elastic lamina means comprises a pair of mutually-facing elastic laminae, each of said elastic laminae comprising a respective slot for coupling with one of said at least one bulge.

12. A device for transcutaneous biopsy of rigid tissues comprising:
    (a) needle means comprising a substantially cylindrical first hollow body omprising a distal end, a mouth and a cutting edge at said distal end, a substantially constant inner diameter, and at least one bulge extending toward an inside portion of said first hollow body;
    (b) blocking means comprising a substantially cylindrical second hollow body having an inner diameter and being slidably coupled inside said needle means for blocking a sample of tissue inside said needle means;
    wherein the distal end of said first hollow body ends with a narrowed portion dimensioned so that said mouth has a diameter substantially corresponding to the inner diameter of said second hollow body.

13. A device for transcutaneous biopsy of rigid tissues comprising:
    (a) needle means comprising a distal end, a cutting edge at said distal end, and a substantially cylindrical hollow body having a substantially constant inner diameter; and
    (b) blocking means slidably coupled inside said needle means for blocking a sample of tissue inside said needle means, said blocking means comprising at least one elastic lamina means;
    wherein said at least one elastic lamina means is provided with a bulge and said substantially cylindrical hollow body comprises a respective slot for coupling with said bulge;
    said blocking means being slidable inside said needle means between a first position wherein said bulge is inserted into said slot and a second position wherein said bulge is completely inside the needle means.

* * * * *